United States Patent
Baileykobayashi et al.

(10) Patent No.: US 9,856,293 B2
(45) Date of Patent: Jan. 2, 2018

(54) METHODS FOR INDUCING NESTIN EXPRESSION OF ASTROCYTES BY NESTIN-INDUCING SYNTHETIC PEPTIDES DERIVED FROM THE BC-BOX OF THE SOCS6 PROTEIN

(71) Applicant: TOAGOSEI CO. LTD., Tokyo (JP)

(72) Inventors: Nahoko Baileykobayashi, Tsukuba (JP); Tetsuhiko Yoshida, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

(21) Appl. No.: 15/028,668

(22) PCT Filed: Oct. 10, 2014

(86) PCT No.: PCT/JP2014/077176
§ 371 (c)(1),
(2) Date: Apr. 11, 2016

(87) PCT Pub. No.: WO2015/053388
PCT Pub. Date: Apr. 16, 2015

(65) Prior Publication Data
US 2016/0257714 A1     Sep. 8, 2016

(30) Foreign Application Priority Data
Oct. 11, 2013   (JP) ................. 2013-213943

(51) Int. Cl.
| | | |
|---|---|---|
| *C12N 5/079* | (2010.01) |
| *C12N 5/02* | (2006.01) |
| *C12N 5/07* | (2010.01) |
| *C12N 5/071* | (2010.01) |
| *C12N 5/074* | (2010.01) |
| *C12N 5/0735* | (2010.01) |
| *C12N 5/0789* | (2010.01) |
| *C12N 5/0793* | (2010.01) |
| *C12N 5/0797* | (2010.01) |
| *C12N 5/00* | (2006.01) |
| *A61K 38/00* | (2006.01) |
| *C07K 7/00* | (2006.01) |
| *C07K 7/08* | (2006.01) |
| *C07K 14/47* | (2006.01) |
| *C07K 14/00* | (2006.01) |

(52) U.S. Cl.
CPC ............ *C07K 7/08* (2013.01); *C07K 14/00* (2013.01); *C07K 14/47* (2013.01); *C12N 5/0622* (2013.01); *A61K 38/00* (2013.01); *C07K 2319/00* (2013.01); *C12N 2533/50* (2013.01)

(58) Field of Classification Search
CPC .... A61K 2300/00; A61K 35/12; A61K 35/30; A61K 35/51; A61K 35/28; A61K 2035/124; A61K 35/545; A61K 38/00; A61K 38/1709; C12N 2506/02; C12N 2502/02; C12N 5/0605; C12N 5/0623; C12N 2506/03; C12N 2533/50; C12N 5/0619; C12N 5/0647; C12N 2509/00; C12N 2533/90; C12N 5/0618; C12N 5/0622; C12N 5/0662; C12N 5/0667; C12N 2502/03; C12N 2502/08; C12N 2506/025; C12N 5/0692; C12N 5/0695; C12N 5/0669; G01N 33/5073; G01N 33/5058; G01N 2800/52; G01N 2500/10; G01N 33/6896; A61L 2430/32; A61L 27/383; A61L 27/3834; C07K 14/00
See application file for complete search history.

(56) References Cited

U.S. PATENT DOCUMENTS

| | | | |
|---|---|---|---|
| 2009/0030179 A1 | 1/2009 | Yoshida et al. | |
| 2009/0253618 A1 | 10/2009 | Kanno et al. | |
| 2010/0297758 A1* | 11/2010 | Yoshida ............... | C07K 7/08 435/366 |
| 2012/0208752 A1 | 8/2012 | Yoshida et al. | |

FOREIGN PATENT DOCUMENTS

| | | | | |
|---|---|---|---|---|
| EP | 1849474 | * | 2/2006 | ............ A61K 38/00 |
| WO | 2006/088010 A1 | | 8/2006 | |
| WO | WO2006/088010 | * | 8/2006 | ............ A61K 38/00 |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Sawamoto, Kazunobu, "Endogenous repair mechanisms in the brain", Clinical Neurology, 2009, vol. 49, No. 11, pp. 330-833.
Aguado, Tania et al., "The Endocannabinoid System Promotes Astroglial Differentiation by Acting on Neural Progenitor Cells", The Journal of Neuroscience, Feb. 1, 2006, vol. 26, No. 5, pp. 1551-1561.
Alvarez-Buylla, Arturo et al., "For the Long Run: Maintaining Germinal Niches in the Adult Brain", Neuron, Mar. 4, 2004, vol. 41, pp. 683-686.

(Continued)

*Primary Examiner* — Chang-Yu Wang
(74) *Attorney, Agent, or Firm* — Oliff PLC

(57) ABSTRACT

A synthetic peptide having nestin expression inducing ability which allows induction of expression of nestin in astrocytes; an agent for inducing nestin expression including the peptide as an active ingredient; and a method for producing high nestin expressing cells derived from astrocytes, the method being characterized in that the agent for inducing nestin expression is supplied. The agent for inducing nestin expression provided by the present invention includes, as an active ingredient, a synthetic peptide including a nestin-inducing peptide sequence consisting of an amino acid sequence of SEQ ID NO: 1 or an amino acid sequence formed by conservative replacement of 1, 2 or 3 amino acid residues in the amino acid sequence. The method for producing high nestin expressing cells derived from astrocytes provided by the present invention includes preparing an astrocyte culture, and supplying, at least once, the agent for inducing nestin expression to the astrocyte culture.

7 Claims, 3 Drawing Sheets

(56) References Cited

FOREIGN PATENT DOCUMENTS

| WO | 2007/010989 A1 | 1/2007 |
| WO | 2009/093692 A1 | 7/2009 |
| WO | 2011/052679 A1 | 5/2011 |

OTHER PUBLICATIONS

Kempermann, Gerd et al., "Milestones of neuronal development in the adult hippocampus", Trends in Neurosciences, Aug. 2004, vol. 27, No. 8, pp. 447-452.

Seri, Bettina et al., "Astrocytes Give Rise to new Neurons in the Adult Mammalian Hippocampus", The Journal of Neuroscience, Sep. 15, 2001, vol. 21, No. 18, pp. 7153-7160.

Laywell, Eric D. et al., "Identification of a multipotent astrocytic stem cell in the immature and adult mouse brain", PNAS, Dec. 5, 2000, vol. 97, No. 25, pp. 13883-13888.

Chouchane, Melek et al., "Cell therapy for stroke: use of local astrocytes", Frontiers in Cellular Neuroscience, Oct. 31, 2012, vol. 6, Article 49, pp. 1-6.

Jan. 13, 2015 Search Report issued in International Patent Application No. PCT/JP2014/077176.

Hwang, Mi-Na et al., "The nuclear localization of SOCS6 requires the N-terminal region and negatively regulates Stat3 protein levels", Biochemical and Biophysical Research Communications, 2007, vol. 360, pp. 333-338.

Cao, Fang et al., "Overexpression of SOCS3 inhibits astrogliogenesis and promotes maintenance of neural stem cells", Journal of Neurochemistry, 2006, vol. 98, pp. 459-470.

Hilton, Douglas J. et al., "Twenty proteins containing a C-terminal SOCS box form five structural classes", Proc. Natl. Acad. Sci. USA, Jan. 1998, vol. 95, pp. 114-119.

Apr. 12, 2016 International Preliminary Report on Patentability issued in International Patent Application No. PCT/JP2014/077176.

\* cited by examiner

FIG.3
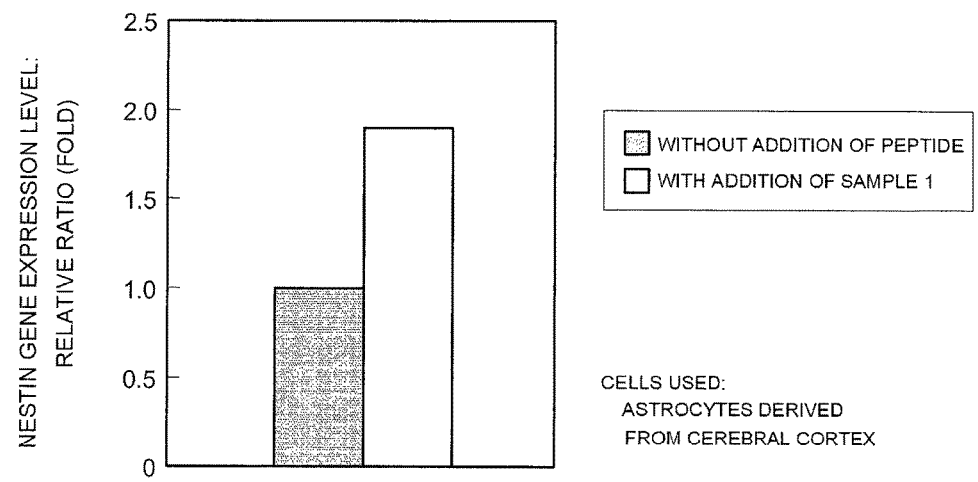
FIG. 4
FIG.4
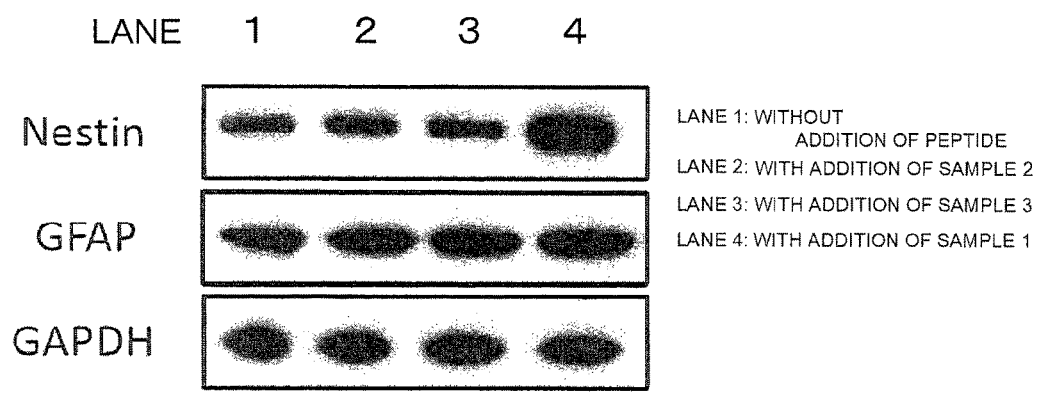

```
SEQUENCE LISTING

<160> NUMBER OF SEQ ID NOS: 13

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

<400> SEQUENCE: 1

Ser Leu Gln Tyr Leu Cys Arg Phe Val Ile Arg Gln Tyr Thr Arg
1               5                   10                  15

<210> SEQ ID NO 2
<211> LENGTH: 13
<212> TYPE: PRT
<213> ORGANISM: Artificial sequence
<220> FEATURE:
<223> OTHER INFORMATION: Synthetic peptide

<400> SEQUENCE: 2

Lys Lys Arg Thr Leu Arg Lys Asn Asp Arg Lys Lys Arg
1               5                   10

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Trp Arg Arg Gln Ala Arg Phe Lys
1               5

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Tyr Gly Arg Lys Lys Arg Arg Gln Arg Arg Arg
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Tyr Ala Arg Ala Ala Ala Arg Gln Ala Arg Ala
1               5                   10
```

```
<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 28
<212> TYPE: PRT
<213> ORGANISM: Artificial sequence
<220> FEATURE:
<223> OTHER INFORMATION: Synthetic peptide

<400> SEQUENCE: 7

Ser Leu Gln Tyr Leu Cys Arg Phe Val Ile Arg Gln Tyr Thr Arg Lys
1               5                   10                  15

Lys Arg Thr Leu Arg Lys Asn Asp Arg Lys Lys Arg
            20                  25

<210> SEQ ID NO 8
<211> LENGTH: 28
<212> TYPE: PRT
<213> ORGANISM: Artificial sequence
<220> FEATURE:
<223> OTHER INFORMATION: Synthetic peptide

<400> SEQUENCE: 8

Asn Leu Gln Asp Leu Cys Arg Ile Lys Ile Arg Gln Cys Ile Gly Lys
1               5                   10                  15

Lys Arg Thr Leu Arg Lys Asn Asp Arg Lys Lys Arg
            20                  25

<210> SEQ ID NO 9
<211> LENGTH: 28
<212> TYPE: PRT
<213> ORGANISM: Artificial sequence
<220> FEATURE:
<223> OTHER INFORMATION: Synthetic peptide

<400> SEQUENCE: 9

Thr Leu His Gln Gln Cys Ile Arg Val Leu Lys Asn Asn Ile Asp Lys
1               5                   10                  15

Lys Arg Thr Leu Arg Lys Asn Asp Arg Lys Lys Arg
            20                  25

<210> SEQ ID NO 10
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 10
gtccttagtc tggaggtggc taca                                          24

<210> SEQ ID NO 11
<211> LENGTH: 24
<212> TYPE: DNA
<213> ORGANISM: Artificial sequence
<220> FEATURE:
```

```
<223> OTHER INFORMATION: Synthetic nucleotide

<400> SEQUENCE: 11
ccaggtgtct gcaaccgaga gttc                                      24

<210> SEQ ID NO 12
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 12
cctggctcct agcaccatga ag                                        22

<210> SEQ ID NO 13
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 13
gatagagcca ccaatccaca cag                                       23
```

METHODS FOR INDUCING NESTIN EXPRESSION OF ASTROCYTES BY NESTIN-INDUCING SYNTHETIC PEPTIDES DERIVED FROM THE BC-BOX OF THE SOCS6 PROTEIN

This application is the U.S. national phase of PCT Application No. PCT/JP2014/077176 filed Oct. 10, 2014, and claims priority to Japanese Patent Application No. 2013-213943 filed Oct. 11, 2013.

TECHNICAL FIELD

The present invention relates to a synthetic peptide that can induce expression of nestin or increase the expression level of nestin in astrocytes, and use thereof. Particularly, the present invention relates to an agent (composition) for inducing expression of nestin including the peptide as an active ingredient and a method for producing cells expressing a high level of nestin derived from astrocytes by using the peptide.

The present application claims the priority to Japanese Patent Application No. 2013-213943 filed on 11 Oct. 2013, which is incorporated herein by reference in its entirety.

BACKGROUND ART

One of the challenges that regenerative therapy faces is regeneration and restoration of nerve function damaged by various nervous system diseases, trauma and the like.

For example, a method is sought in which neuronal cells generated by in vitro culture systems are injected into affected sites to complement lost neuronal cells. However, even when neuronal cells which have already extended neuroaxes are injected to affected sites (such as the central nerve system tissue including brain), it is difficult to reconstruct the neural network as prior to being damaged. In addition, the central nerve system tissue particularly exhibits and maintains nerve functions by constituting the physiological environment in which neuronal cells and various other cells (such as astrocytes) interact, and thus it is difficult to restore the nerve function only by compensation of the neuronal cells.

Consequently, it is expected to establish the regeneration and restoration techniques of nerve function by utilizing neural stem cells. For example, it is expected to restore the nerve function by a therapeutic method in which neural stem cells are injected to affected sites (such as the central nerve system tissue including brain) or regeneration ability of the endogenous neural stem cells is utilized to allow differentiation in vivo (typically at the affected sites) of the stem cells to required cells (such as neuronal cells and astrocytes), thereby compensating lost cells and reconstructing the neural network and physiological environment.

It has been recently demonstrated that neural stem cells exist in the adult brain and when the brain is damaged, neuronal cells differentiated from the neural stem cells migrate towards the affected site (damaged site) and the neuronal cells grow at the affected site to mature neuronal cells to contribute to compensation of neuronal cells and reconstruction of the neural network (Non Patent Literature 1). However, differentiation of neural stem cells to neuronal cells in the adult brain has only been demonstrated in limited regions such as the subventricular zone (SVZ) region of the lateral ventricle or the subgranular zone (SGZ) region of the hippocampal dentate gyrus. It is also pointed out that the number of neural stem cells in the adult brain is low and the number of surviving neuronal cells differentiated from neural stem cells and migrated to the affected site is extremely low. From this reason, it is insufficient to regenerate and restore the nerve function only by spontaneous supply of neuronal cells by neural stem cells in the adult brain as described above. At present, no efficient means has been established that promotes in vivo differentiation of neural stem cells existing in the adult brain to required cells, migration of the cells to the affected site and further engraftment thereof at the affected site.

Meanwhile, neural stem cells injectable to affected sites may be obtained by methods such as the one in which neural stem cells in the foetal brain or in the early postnatal brain or neural stem cells in the adult brain are utilized or the one in which embryonic stem cells (ES cells) or induced pluripotent stem cells (iPS cells) are differentiated. However, the method utilizing neural stem cells in the brain or the method for differentiating ES cells have difficulties in terms of ethical problems and rejections. The method for differentiating induced pluripotent stem cells also has many challenges in terms of safety, efficiency and costs for practical application.

CITATION LIST

Patent Literature

[Patent Literature 1] WO 2009/093692

Non Patent Literature

[Non Patent Literature 1] Rinsho Shinkeigaku (Clinical Neurology), Vol. 49 (No. 11), 2009, pp. 830-833
[Non Patent Literature 2] The Journal of Neuroscience, Vol. 26 (No. 5), 2006, pp. 1551-1561
[Non Patent Literature 3] Neuron, Vol. 41 (No. 5), 2004, pp. 683-686
[Non Patent Literature 4] TRENDS in Neurosciences, Vol. 27 (No. 8), 2004, pp. 447-452
[Non Patent Literature 5] The Journal of Neuroscience, Vol. 21 (No. 18), 2001, pp. 7153-7160
[Non Patent Literature 6] PNAS, Vol. 97 (No. 25), 2000, pp. 13883-13888
[Non Patent Literature 7] Frontiers in Cellular Neuroscience, Vol. 6, 2012, pp. 1-6

SUMMARY OF INVENTION

It has been recently demonstrated that in the SVZ and SGZ regions, a cell population which expresses a marker protein of neural stem cells, nestin, and has characteristic properties of astrocytes is pluripotent and produces neuronal cells, namely the cells in the population form a population of neural stem cells in the adult brain (Non Patent Literatures 2 to 6). It has also been demonstrated that the neural stem cells co-express nestin and a marker protein of astrocytes, glial fibrillary acidic protein (GFAP). Accordingly, it is expected to establish the technique for inducing expression of nestin or increasing the expression level of nestin in astrocytes, thereby generating (producing) neural stem cells from the astrocytes (in other words, dedifferentiating or inducing dedifferentiation of astrocytes).

Astrocytes widely exist in the central nerve system and the number thereof is high. Therefore, in vivo or in vitro generation of neural stem cells from astrocytes (in other words, an increase in the expression level of nestin in astrocytes or generation of high nestin expressing cells derived from astrocytes) has a great potential in medical industries, if such generation is feasible. However, there is no established method for efficiently producing high nestin expressing cells derived from astrocytes in a short time, and thus there is a need for establishment of such a method and development of an agent for inducing nestin expression used for the purpose. In addition, from the same reason, there is a need for establishment of a method for producing neural stem cells by increasing the expression level of nestin in astrocytes. Non Patent Literature 7, for example, discloses a method for inducing (transdifferentiating) particular neuronal cells from astrocytes by forcing the astrocytes to express a specific gene. However, the document does not disclose a method for producing high nestin expressing cells from astrocytes or a method for producing neural stem cells from astrocytes.

Thus, an object of the present invention is to provide a nestin-inducing synthetic peptide which is a relatively short-chain, artificially synthesised peptide and can increase the expression level of nestin in astrocytes. Another object of the present invention is to provide a method for producing high nestin expressing cells derived from astrocyte by using the peptide. Another object of the present invention is to provide an agent (pharmaceutical composition) for inducing nestin expression having the peptide as an active ingredient.

The inventor of the present invention extensively studied peptides having known amino acid sequences and having identified functions in cells or amino acid sequences of the partial peptides (namely motifs having identified functions) and thus focused on peptides having amino acid sequences included in BC-boxes of various proteins identified as SOCS (suppressor of cytokine signalling) proteins. The SOCS proteins used herein collectively refer to various SOCS proteins and proteins belonging to the family which have an SOCS-box, a region (amino acid sequence) that can bind to the Elongin BC complex (specifically a part of Elongin C) which is known to form a complex with Elongin A to serve as a transcription regulatory factor. The BC-box used herein refers to a specific region which is believed to bind to the Elongin BC complex.

As a result of extensive studies, the inventor found that a synthetic peptide constructed by using a whole or partial amino acid sequence of the BC-box of the SOCS6 protein has an excellent ability for inducing nestin expression (nestin expression inducing activity) in astrocytes (in other words, increasing the expression level of nestin in astrocytes), thereby completing the present invention.

In order to achieve the above-mentioned objectives, the present invention provides an agent for inducing nestin expression used for increasing the expression level of nestin in astrocytes, characterized in that the agent includes, as an active ingredient (namely a substance involved in an increase of the expression level of nestin in astrocytes), at least one peptide (hereinafter referred to as "nestin-inducing synthetic peptide") having an ability to induce nestin expression of astrocytes or promote induction of nestin expression of astrocytes (in other words, to increase nestin expression or promote an increase in nestin expression) when the agent is supplied to at least one astrocyte culture (typically into a medium).

Namely, the nestin-inducing synthetic peptide according to the present invention which can be used as an active ingredient of the agent for inducing nestin expression is a synthetic peptide including, in the peptide chain thereof, a nestin-inducing peptide sequence consisting of the following amino acid sequence:

(SEQ ID NO: 1)
SLQYLCRFVIRQYTR;

or an amino acid sequence formed by conservative replacement of 1, 2 or 3 amino acid residues in the above amino acid sequence.

Typically, the agent for inducing nestin expression contains at least one pharmaceutically acceptable carrier (such as at least one substrate contributing to an improvement in stability of the peptide or a liquid medium including saline and various buffers).

The nestin-inducing synthetic peptide described herein can be readily and artificially produced by chemical synthesis (or biosynthesis). In addition, the peptide per se has a simple structure (linear peptide chain), and thus is easily handled. By such a simple process that, for example, adding the synthetic peptide into an astrocyte culture (typically into a medium), induction of nestin expression or an increase in the expression level of nestin in the astrocytes can be realised.

In a preferred embodiment of the agent for inducing nestin expression described herein, the nestin-inducing synthetic peptide comprises a membrane-penetrating peptide sequence N-terminal or C-terminal to the amino acid sequence of the nestin-inducing peptide sequence.

By adding the nestin-inducing synthetic peptide having the membrane-penetrating peptide sequence to desired astrocytes, the nestin-inducing peptide sequence can be highly effectively transferred from outside of the astrocytes (typically from outside of the cell membrane) to inside of the cells.

In a preferred embodiment of the agent for inducing nestin expression described herein, the nestin-inducing synthetic peptide comprises the membrane-penetrating peptide sequence consisting of the following amino acid sequence:

(SEQ ID NO: 2)
KKRTLRKNDRKKR.

The amino acid sequence described herein under SEQ ID NO: 2 is a typical example of the amino acid sequence included in membrane-penetrating peptides and can be suitably used for the present invention.

In another preferred embodiment of the agent for inducing nestin expression described herein, the nestin-inducing synthetic peptide has 28 or less amino acid residues in total. The peptide having such a short chain is easily obtained by chemical synthesis, is inexpensive and is easily handled, and thus is preferable as a component of the agent for inducing nestin expression.

In another preferred embodiment of the agent for inducing nestin expression described herein, the nestin-inducing synthetic peptide comprises the following amino acid sequence:

(SEQ ID NO: 7)
SLQYLCRFVIRQYTRKKRTLRKNDRKKR.

The agent for inducing nestin expression including such a nestin-inducing synthetic peptide is particularly suitable for increasing the expression level of nestin in astrocytes derived from humans or a mammal other than humans.

In another aspect, the present invention provides a method for producing high nestin expressing cells derived from astrocytes or for improving productivity of the high nestin expressing cells, characterized in that the method comprises preparing an astrocyte culture and supplying, at least once, any of nestin-inducing synthetic peptides described herein (in other words, the agent for inducing nestin expression including any of the nestin-inducing synthetic peptides described herein), to the astrocyte culture.

According to the method, high nestin expressing cells derived from astrocytes can be efficiently produced by such a simple process that the simple synthetic peptide is used as a nestin expression inducing factor. The method can be suitably used in astrocyte particularly derived from humans or a mammal other than humans.

Another preferable embodiment of the method for producing high nestin expressing cells described herein further comprises selecting high nestin expressing cells from the astrocyte culture to which the nestin-inducing synthetic peptide has been supplied at least once.

According to the method, a population of high nestin expressing cells having high purity can be produced.

Another preferable embodiment of the method for producing high nestin expressing cells described herein comprises selecting the high nestin expressing cells by using a cell sorter.

According to the method, high nestin expressing cells can be selected with high efficiency. Such a method is particularly suitable for production of high nestin expressing cells at high amount and at high purity.

The method for producing the high nestin expressing cells derived from astrocytes as described herein can be suitably used for producing neural stem cells derived from astrocytes. Namely, by increasing the expression level of nestin in astrocytes, neural stem cells expressing nestin (nestin-expressing neural stem cell) can be produced. It is demonstrated in Non Patent Literatures 1 to 6 that cells which express nestin and have characteristic properties of astrocytes serve as neural stem cells in the adult brain.

The nestin-inducing synthetic peptide described herein can be suitably practiced as a synthetic peptide having astrocyte-dedifferentiating ability (also referred to as an astrocyte-dedifferentiating synthetic peptide) which can dedifferentiate or promote dedifferentiation of astrocytes to nestin-expressing neural stem cells by increasing the expression level of nestin in astrocytes. The agent for inducing nestin expression including the nestin-inducing synthetic peptide as an active ingredient can be similarly practised as an agent for dedifferentiating astrocytes.

BRIEF DESCRIPTION OF DRAWINGS

FIG. 3 is a graph showing expression of the nestin gene in astrocytes derived from the cerebral cortex cultured by adding a sample peptide (sample 1) according to one embodiment expressed as a result of qRT-PCR.

FIG. 4 is an image showing expression of nestin in astrocytes derived from the cerebral cortex cultured by adding any of a sample peptide (sample 1) according to one embodiment and comparative sample peptides (samples 2 to 3) expressed as a result of western blot analysis.

DESCRIPTION OF EMBODIMENTS

Figure 1:
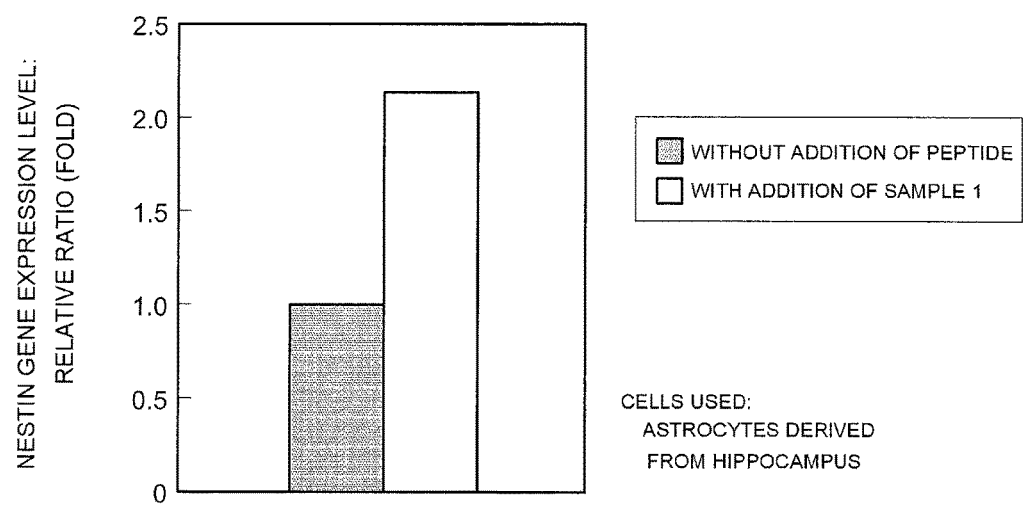
FIG. 1 is a graph showing expression of the nestin gene in astrocytes derived from the hippocampus cultured by adding a sample peptide (sample 1) according to one embodiment expressed as a result of quantitative reverse transcriptase-polymerase chain reaction (also referred to as qRT-PCR).

Preferred embodiments of the present invention are described below. Note that matters other than the matters particularly mentioned in the present description (e.g. primary structures or chain length of synthetic peptides described herein) which are required for carrying out the present invention (e.g. general matters relating to peptide chemical synthesis, cell culture and preparation of a pharmaceutical composition including a peptide) are matters of design variation that could be apprehended by a person skilled in the art based on conventional art in such fields as cell engineering, physiology, medical science, pharmaceutical science, organic chemistry, biochemistry, gene engineering, protein engineering, molecular biology, genetics and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The entire contents of all publications cited herein are incorporated in the present specification by reference.

In the present description, the term "synthetic peptide" refers to a peptide chain which does not stably exists by itself in nature, and is instead a peptide fragment that is manufactured by artificial chemical synthesis or biosynthesis (i.e. genetic engineering based production) and may stably exist in a certain composition (e.g. an agent for inducing nestin expression).

In the present description, the term "peptide" denotes an amino acid polymer having a plurality of peptide bonds. The term is not limited by the number of amino acid residues in a peptide chain, and refers to a chain having relatively small molecular weight typically including the one having about 100 or less (preferably 60 or less, for example 50 or less) amino acid residues in total.

In the present description, unless otherwise specified, the term "amino acid residue" includes the N-terminal amino acid and the C-terminal amino acid of a peptide chain.

The amino acid sequences described herein are always denoted as N-terminal on the left side and C-terminal on the right side.

In the present description, the term "modified amino acid sequence" with regard to a prescribed amino acid sequence refers to an amino acid sequence obtained by substituting, deleting and/or adding (inserting) one or a few (e.g. 2 or 3) amino acid residues without a loss of the function of the prescribed amino acid sequence (e.g. nestin expression inducing ability of the nestin-inducing synthetic peptide). Typical examples encompassed by such modified amino acid sequence as used herein include a sequence obtained by so-called conservative amino acid replacement, i.e. conservative substitution, of 1 or a few (typically 2 or 3) amino acid residues (e.g. a sequence wherein a basic amino acid residue has been replaced with another basic amino acid residue: e.g. replacement between a lysine residue and an arginine residue), or a sequence wherein 1 or a few (typically 2 or 3) amino acid residues are added (inserted) or deleted to/from a prescribed amino acid sequence. Accordingly, the nestin-inducing synthetic peptide described herein encompasses synthetic peptides having identical amino acid sequences as those represented by corresponding SEQ ID NOs as well as synthetic peptides having amino acid sequences wherein 1 or a few (typically 2 or 3) amino acid residues are replaced (e.g. conservative amino acid replacement as described above), deleted and/or added in/from/to amino acid sequences represented by SEQ ID NOs and which still exhibit the nestin expression inducing ability.

In the present description, the term "polynucleotide" denotes a polymer (nucleic acids) of a plurality of nucleotides linked via phosphodiester bonds and is not limited by the number of nucleotides. The polynucleotide as used herein encompasses DNA fragments and RNA fragments having various length. The term "artificially designed polynucleotide" refers to a polynucleotide whose chain (full length) does not exist by itself in nature and that is artificially synthesised by chemical synthesis or biosynthesis (i.e. genetic engineering based production).

In the present description, "nestin" is a protein which is recognised as a marker protein of neural stem cells. Namely, high nestin expressing cells derived from astrocytes may function as neural stem cells. Astrocytes in vivo generally do not express nestin. However, cultured cells may weakly express nestin even without stimulation.

In the present description, the term "neural stem cell" refers to a cell that has self-replication competence and can be differentiated into one or more, preferably two or more types of neural cells (typically neuronal cells or glial cells) or tissues containing the cells. In the present description, neural stem cells may be cells characterized by expression of nestin; however the feature does not limit the neural stem cells as far as the neural stem cells have the abilities described above.

In the present description, "dedifferentiation" refers to transition of cells which have been already differentiated (differentiated cells) to the status thereof before differentiation by losing characteristics and functions of the differentiated cells. For example, dedifferentiation may refer to transition of neuronal cells to neural progenitor cells, neural stem cells or pluripotent stem cells and is a concept also encompassing "initialisation" of differentiated cells. The term "astrocyte dedifferentiation" particularly refers to transition of astrocytes to the status of cells having functions of neural stem cells, i.e. transition of astrocytes to neural stem cells by inducing expression of nestin in the astrocytes.

A method for producing high nestin expressing cells derived from astrocytes as described herein is characterized in that an astrocyte culture is prepared and a synthetic peptide having a nestin-inducing peptide sequence (SEQ ID NO: 1) (i.e. a nestin-inducing synthetic peptide), which has been found by the inventor of the present invention to have an ability of increasing the expression level of nestin (in other words, an ability of inducing nestin expression) in astrocytes upon addition thereof to astrocytes, is supplied at least once to the astrocyte culture (typically into a medium).

Suitable examples of the astrocytes include astrocytes derived from humans or an animal other than humans (typically a mammal). The nestin-inducing synthetic peptide described herein may particularly increase the expression level of nestin or promote an increase in the expression level in astrocytes derived from humans.

As described above, the nestin-inducing synthetic peptide described herein is a synthetic peptide having the nestin-inducing peptide sequence (SEQ ID NO: 1) or a modified amino acid sequence thereof. The specific amino acid sequence represented by SEQ ID NO: 1 is a partial peptide chain (amino acid sequence) constituting a BC-box of human SOCS6 and is an amino acid sequence consisting of 15 consecutive amino acid residues from the N-terminal of the BC-box, as well as is a sequence which is found by the inventor of the present invention to induce nestin expression or increase the expression level of nestin in at least one type of astrocytes. Despite recent studies on signal peptide functions, no document suggests that the SOCS6 signal sequence is used to induce nestin expression in at least one type of astrocytes.

The nestin-inducing synthetic peptide described herein may be a synthetic peptide solely consisting of the nestin-inducing peptide sequence (including modified amino acid sequences) represented by SEQ ID NO: 1. However, in view of improving nestin expression inducing ability, a synthetic peptide preferably has a membrane-penetrating peptide sequence N-terminal or C-terminal to the nestin-inducing peptide sequence. When the peptide is applied to target astrocyte, the synthetic peptide having the membrane-penetrating peptide sequence can be readily introduced into target astrocytes and thus can have an improved nestin expression inducing ability.

Any membrane-penetrating peptide sequence used is not particularly limited as far as it is an amino acid sequence constituting a membrane-penetrating peptide that can penetrate cell membrane and/or nuclear membrane. Among various suitable known membrane-penetrating peptide sequences, the membrane-penetrating peptide sequence of the nestin-inducing synthetic peptide preferably has an amino acid sequence (including modified amino acid sequences) relating to NoLSs (nucleolar localization signals). Examples thereof include amino acid sequences of the NoLS represented by SEQ ID NO: 2 in LIM kinase 2 and the NoLS represented by SEQ ID NO: 3 in the N protein (nucleocapsid protein) of IBV (avian infectious bronchitis virus), and peptides comprising the amino acid sequences. Other examples of the membrane-penetrating peptide sequence include amino acid sequences represented by SEQ ID NOs: 4 to 6 and modified amino acid sequences thereof (only those retaining membrane-penetrating ability). SEQ ID NO: 4 represents an amino acid sequence of a membrane-penetrating peptide sequence in TAT of HIV (Human Immunodeficiency Virus) and a peptide comprising the sequence. SEQ ID NO: 5 represents an amino acid sequence of a membrane-penetrating peptide sequence obtained by modification of TAT (PTD4) and a peptide comprising the sequence. SEQ ID NO: 6 represents an ANT-related amino acid sequence of Antennapedia, which is a mutant from *Drosophila*, and a peptide comprising the sequence.

Above membrane-penetrating peptide sequences indicated also in the sequence listing are merely examples and do not limit the peptide sequences which may be used. Various membrane-penetrating peptide sequences which may be used for the present invention are disclosed in numerous references which are already published at the time of filing of the present application. Amino acid sequences of the membrane-penetrating peptide sequences are readily known by common search means.

Particularly, the membrane-penetrating peptide sequence is preferably the following amino acid sequence:

(SEQ ID NO: 2)
KKRTLRKNDRKKR.

The combination of the amino acid sequence represented by SEQ ID NO: 2 or a modified amino acid sequence thereof and the nestin-inducing peptide sequence (SEQ ID NO: 1) or a modified amino acid sequence thereof allows provision of a synthetic peptide exhibiting high nestin expression inducing ability.

The nestin-inducing synthetic peptide described herein particularly preferably includes the following amino acid sequence:

(SEQ ID NO: 7)
SLQYLCRFVIRQYTRKKRTLRKNDRKKR;

or a modified amino acid sequence thereof. The amino acid sequence represented by SEQ ID NO: 7 is the amino acid sequence consisting of 28 amino acid residues in total constituted by combining the amino acid sequence constituting human SOCS6 signal sequence represented by SEQ ID NO: 1 and the amino acid sequence derived from LIM kinase 2 represented by SEQ ID NO: 2.

Some peptide chains (amino acid sequences) of the nestin-inducing synthetic peptide described herein may be constituted by appropriately combining the nestin-inducing peptide sequence and the membrane-penetrating peptide sequence described above. Any of the nestin-inducing peptide sequence and the membrane-penetrating peptide sequence may be arranged relatively at the C-terminal side (the N-terminal side). It is preferable that the nestin-inducing peptide sequence and the membrane-penetrating peptide sequence are arranged adjacent. Namely, it is preferred that no or 1 to 3 amino acid residues, if any, intervene between the nestin-inducing peptide sequence and the membrane-penetrating peptide sequence. For example, 1 or a few (typically 2 or 3) amino acid residues (e.g. 1 or a few glycine (G) residues) functioning as a linker may be included between the nestin-inducing peptide sequence and the membrane-penetrating peptide sequence.

The nestin-inducing synthetic peptide described herein preferably has at least one amidated amino acid residue. Amidation of a carboxyl group of an amino acid residue (typically a C-terminal amino acid residue of a peptide chain) can improve the structural stability (e.g. protease resistance) of a synthetic peptide.

The nestin-inducing synthetic peptide may contain a partial sequence (amino acid residue) other than amino acid sequences of the nestin-inducing peptide sequence and the membrane-penetrating peptide sequence unless it deteriorates the nestin expression inducing ability. The partial sequence is preferably, but is not limited to, a sequence capable of maintaining three-dimensional shape (typically a linear shape) of the nestin-inducing peptide sequence and membrane-penetrating peptide sequence. The total number of amino acid residues in the peptide chain of the nestin-inducing synthetic peptide is suitably 100 or less, desirably 60 or less and preferably 50 or less. A synthetic peptide having, for example, 30 or less, typically 28 or less amino acid residues is particularly preferred.

Such a short peptide is easily synthesized by chemical synthesis and thus the nestin-inducing synthetic peptide can be easily provided. The conformation of the peptide is not particularly limited as far as the peptide exhibits nestin expression inducing ability in astrocytes in an environment (in vitro or in vivo) where the peptide is used; however, the peptide is preferably linear or helix because such peptide rarely acts as an immunogen (antigen). It is difficult for the peptide having such a shape to form an epitope. In view of this, the nestin-inducing synthetic peptide used for the present invention suitably is linear and has relatively low molecular weight (typically 60 or less, for example 50 or less, particularly 30 or less, specifically 28 or less amino acid residues).

The proportion of the nestin-inducing peptide sequence and the membrane-penetrating peptide sequence relative to the whole amino acid sequence (i.e. % by number of amino acid residues of the nestin-inducing peptide sequence and the membrane-penetrating peptide sequence relative to the total number of amino acid residues of the peptide chain) is not particularly limited unless it deteriorates the nestin expression inducing ability in astrocytes. However, the proportion is desirably about 60% or more, preferably 80% or more and particularly preferably 90% or more. A preferable embodiment is a peptide consisting of the nestin-inducing peptide sequence and the membrane-penetrating peptide sequence (i.e. these sequences account for 100% of the whole amino acid sequence).

The amino acid residues included in the nestin-inducing synthetic peptide of the present invention are preferably all L-amino acids. However, some or all amino acid residues may be substituted with D-amino acids unless it deteriorates nestin expression inducing ability in astrocytes.

The nestin-inducing synthetic peptide described herein can be easily manufactured according to common chemical synthesis methods. For example, conventional solid phase synthesis or liquid phase synthesis may be used. A solid phase synthesis in which an amino protecting group of Boc (t-butyloxycarbonyl) or Fmoc (9-fluorenylmethoxycarbonyl) is used is suitable.

The nestin-inducing synthetic peptide described herein may be synthesised as a desired amino acid sequence having a modified portion (C-terminal amidation and the like) by solid phase synthesis using a commercially available peptide synthesiser (e.g. available from Intavis AG, Protein Technologies and the like).

Alternatively, the nestin-inducing synthetic peptide may be biosynthesised according to genetic engineering. Namely, a polynucleotide (typically DNA) having a nucleotide sequence (including an ATG initiation codon) encoding an amino acid sequence of a desired nestin-inducing synthetic peptide is synthesised. Then, according to a host cell, a recombinant vector is constructed which has an expression gene construct comprising the synthesised polynucleotide (DNA) and various regulation elements (encompassing a promoter, a ribosome-binding site, a terminator, an enhancer and various cis elements controlling expression level) for expressing the amino acid sequence in the host cell.

The recombinant vector is introduced into the host cell (e.g. yeast, insect cells, plant cells) by common technique and the host cell or a tissue or individual including the cell is cultured under a prescribed condition. Thereby a desired peptide may be expressed and produced in cells. The peptide may be isolated from the host cells (from a medium when the peptide is secreted) and optionally refolded and purified to give a desired nestin-inducing synthetic peptide.

Construction of a recombinant vector, introduction of the constituted recombinant vector into a host cell and the like may be carried out by methods conventionally used in the art. As the present invention is not characterized by the methods per se, detailed explanations for the methods are not given herein.

For example, a fusion protein expression system can be used in order to allow efficient production at a high amount in host cells. Thus, a gene (DNA) encoding an amino acid sequence of a desired nestin-inducing synthetic peptide is chemically synthesised, and the synthesised gene is introduced into a suitable site of an appropriate vector for fusion protein expression (e.g. vectors for GST (Glutathione S-transferase) fusion protein expression such as of pET series available from Novagen and of pGEX series available from Amersham Biosciences). A host cell (typically *Escherichia coli*) is then transformed with the vector. The resulting transformant is cultured to prepare a desired fusion protein. The protein is then extracted and purified. The resulting purified fusion protein is then cleaved with a predetermined enzyme (protease) and the released desired peptide fragment (designed nestin-inducing synthetic peptide) is recovered by affinity chromatography or the like. Optionally, refolding may be carried out according to an appropriate method. By using such a conventionally known fusion protein expression system (e.g. a GST/His system available from Amersham Biosciences may be used), the nestin-inducing synthetic peptide described herein may be manufactured.

Alternatively, a desired polypeptide may be synthesized in vitro with a so-called cell-free protein synthesis system by constructing a template DNA (i.e. a synthetic gene fragment including a nucleotide sequence encoding an amino acid sequence of the nestin-inducing synthetic peptide) for a cell-free protein synthesis system and using various compounds (ATP, RNA polymerase, amino acids and the like) required for peptide synthesis. With regard to cell-free protein synthesis systems, publications by Shimizu et al. (Shimizu et al., Nature Biotechnology, 19, 751-755 (2001)) and by Madin et al. (Madin et al., Proc. Natl. Acad. Sci. USA, 97(2), 559-564 (2000)) may be referred. Based on the techniques disclosed in the publications, many companies have already provided custom polypeptide production at the time of filing of the present application. In addition, cell-free protein synthesis kits are commercially available (e.g. a PROTEIOS™ Wheat germ cell-free protein synthesis kit available from Toyobo Co., Ltd., Japan).

A single- or double-stranded polynucleotide including a nucleotide sequence encoding the nestin-inducing synthetic peptide described herein and/or a complementary nucleotide sequence thereof may be readily manufactured (synthesised) according to conventionally well-known methods. Namely, a nucleotide sequence corresponding to an amino acid sequence of the nestin-inducing synthetic peptide may be readily determined and provided by selecting codons corresponding to the amino acid residues of the designed amino acid sequence. Once the nucleotide sequence is determined, a polynucleotide (single strand) corresponding to the desired nucleotide sequence may be readily obtained by using a DNA synthesiser and the like. The resulting single-stranded DNA may be then used as a template to obtain a desired double-stranded DNA by employing various enzymatic synthesis means (typically PCR). The polynucleotide may be in the form of DNA or RNA (such as mRNA). DNA may be provided as a double or single strand. When DNA is a single strand, it may be a coding strand (sense strand) or a non-coding strand (anti-sense strand) complementary to the coding strand.

The thus obtained polynucleotide may be used as a material for constructing a recombinant gene (expression cassette) for producing the nestin-inducing synthetic peptide in various host cells or by cell-free protein synthesis systems described above.

The nestin-inducing synthetic peptide described herein may be in the form of a salt unless it deteriorates nestin expression inducing ability in astrocytes. For example, an acid addition salt of the peptide obtained by addition reaction with an inorganic acid or an organic acid which are generally used according to conventional methods may be used. Alternatively, the peptide may be other salts (e.g. a metal salt) as far as nestin expression inducing ability in astrocytes is exhibited. Thus, the "peptide" described herein and in claims encompasses the ones in the form of salts.

The nestin-inducing synthetic peptide described herein is a synthetic peptide having nestin expression inducing ability, and thus can be suitably used for producing high nestin expressing cells derived from astrocytes or for increasing the expression level of nestin in target astrocytes.

The agent for inducing nestin expression described herein may include various pharmaceutically (medically) acceptable carriers depending on the usage forms as far as nestin expression inducing ability of the nestin-inducing synthetic peptide, which is an active ingredient, is retained without elimination. The carrier is preferably the one generally used for peptide medicines such as a diluent and a vehicle. Although it may appropriately vary according to the application and form of the agent for inducing nestin expression, the carrier typically includes water, physiological buffers and various organic solvents. The carrier may be an alcohol (such as ethanol) aqueous solution at an appropriate concentration, glycerol or a non-drying oil such as olive oil. The carrier may alternatively be a liposome. An auxiliary component which may be included in the agent for inducing nestin expression includes various fillers, bulking agents, binding agents, wetting agents, surfactants, dyes, flavours and the like.

The form of the agent for inducing nestin expression is not particularly limited. Examples of the typical form include solutions, suspensions, emulsions, aerosols, foams, granules, powders, tablets, capsules, ointments, water-based gels and the like. The agent may be freeze-dried substances or granules which are dissolved in saline or appropriate buffers (e.g. PBS, namely phosphate buffered saline) immediately prior to use to prepare drug solutions for injections and the like.

The drug (composition) in various forms may be prepared according to conventionally well-known methods from the nestin-inducing synthetic peptide (principal component) and various carriers (auxiliary components). As the present invention is not characterized by such preparation methods per se, detailed explanations for the methods are not given herein. Detailed information on formulation may be found in, for example, Comprehensive Medicinal Chemistry, Corwin Hansch Ed., published by Pergamon Press (1990), the entire content of which is incorporated herein by reference.

Astrocytes for which the agent for inducing nestin expression (nestin-inducing synthetic peptide) described herein is used are not particularly limited, and the agent can induce nestin expression (or promote induction of nestin expression) in astrocytes from various animals. Examples of astrocytes include astrocytes derived from humans or a mammal other than humans. The agent for inducing nestin expression described herein is particularly preferably used for astrocytes from humans.

Astrocytes for which the agent for inducing nestin expression (nestin-inducing synthetic peptide) is used are not limited to cultured cells maintained in vitro and may be astrocytes in vivo.

The agent for inducing nestin expression (nestin-inducing synthetic peptide) described herein may be used as an astrocyte-dedifferentiating agent (astrocyte-dedifferentiating synthetic peptide) which is used for dedifferentiation of astrocytes to nestin-expressing neural stem cells. Namely, the agent for inducing nestin expression (nestin-inducing synthetic peptide) has an astrocyte-dedifferentiating ability.

Suitable examples of the astrocytes are astrocytes derived from humans or an animal (typically a mammal) other than humans. The astrocyte-dedifferentiating agent (astrocyte-dedifferentiating synthetic peptide) described herein can dedifferentiate or promote dedifferentiation of human astrocytes to nestin-expressing neural stem cells.

Astrocytes for which the astrocyte-dedifferentiating agent (astrocyte-dedifferentiating synthetic peptide) is used are not limited to in vitro cultured cells and may be astrocytes in vivo.

Astrocytes in the astrocyte culture described herein are not particularly limited as far as they retain characteristics of astrocytes. Examples thereof may include astrocytes derived from humans or an animal (typically a mammal) other than humans and may include various cultured cells such as primary cultured cells, subcultured cells and cell lines. Astrocytes may be, for example, derived from various tissues in vivo such as glioma, hippocampus, cerebral limbic system, spinal cord and glial cells of peripheral nerve system. Astrocytes may be the one obtained by induction of differentiation of stem cells (e.g. pluripotent stem cells and somatic stem cells) and cells from tissues other than the nerve system (e.g. adipose tissue and skin tissue). Astrocytes obtained by induction of differentiation of various cultured cells derived from the human central nerve system, stem cells and cells from tissues other than the nerve system are preferred in the medical industrial view point.

Astrocytes in the astrocyte culture described herein may be engineered by molecular biological means as far as they retain characteristics thereof. For example, incorporation of telomerase (TERT) gene for establishment of cell lines and incorporation of marker genes for labelling nestin expression or genes encoding marker proteins may be mentioned.

The high nestin expressing cells described herein may be selected according to various cell selection methods without limitation. For example, cell sorting using a fluorescence-activated cell sorter (FACS), cell isolation using a magnetic cell isolation device (MACS®), cell sorting under a microscope, cell sorting using optical forceps, cell sorting using various columns, cell sorting utilizing antigen-antibody reaction, cell sorting utilizing cell staining, cell sorting utilizing labelling by incorporation of specific genes, cell sorting utilizing physiological properties of cells (proliferation, adhesion, migration, characteristic cell division, auxotrophic properties and the like) may be mentioned.

The cell sorter used for selection of the high nestin expressing cells described herein may be any cell sorter without limitation. Examples of the cell sorter include FACS, MACS®, cell sorters utilizing optical forceps and cell sorters utilizing various columns. FACS, MACS and cell sorters utilizing optical forceps can isolate the high nestin expressing cells by automated systems with high efficiency, and thus are suitably used for the present invention. Particularly, FACS and MACS are preferred as they allow isolation with high accuracy.

Examples of the properties of the high nestin expressing cells that can be used for selection of the high nestin expressing cells include nestin, a nestin RNA, a protein highly correlated with the nestin expression or an RNA encoding the protein, or a protein introduced into astrocytes by a molecular biological means or a transcription or translation product of the transgene, or physiological properties of the high nestin expressing cells (proliferation, adhesion, migration, characteristic cell division, auxotrophic properties and the like), or the like. However, the properties are not limited thereto as far as they allow selection of the high nestin expressing cells. Particularly, nestin, a nestin RNA, a protein highly correlated with the nestin expression and an RNA encoding the protein allow identification of expression of nestin by a relatively simple method, and thus are suitably used for the present invention. Particularly, nestin and/or a protein highly correlated with the nestin expression allow identification by antigen-antibody reaction, and thus are preferable. For example, a fluorescent labelled anti-nestin antibody may be used to label a nestin protein, which can then be used as an index to select the high nestin expressing cells.

A method for producing high nestin expressing cells derived from astrocytes described herein can be suitably carried out to produce (generate) nestin-expressing neural stem cells derived from astrocytes. Namely, by increasing the expression level of nestin in astrocytes, neural stem cells highly expressing nestin can be produced.

The method for producing nestin-expressing neural stem cells is not limited to production of neural stem cells in an in vitro culture system, but may also be used for generation of neural stem cells or promotion of generation of neural stem cells in vivo.

An agent for inducing nestin expression (nestin-inducing synthetic peptide) described herein, namely an astrocyte-dedifferentiating agent (astrocyte-dedifferentiating synthetic peptide) can be used in a method and at an amount that are suitable for the form and purpose thereof.

For example, when the expression level of nestin in astrocytes cultured (subcultured) in vitro is to be increased, an appropriate amount of the agent for inducing nestin expression (nestin-inducing synthetic peptide) described herein, namely the astrocyte-dedifferentiating agent (astrocyte-dedifferentiating synthetic peptide) may be added to a medium of the astrocytes at any stage (preferably at an early stage after initiation of the culture) during the culture. The amount and frequency of addition are not particularly limited and may vary according to the type of cultured cells, the cell density (cell density at the time of initiation of the culture), the passage number, the culture conditions, the type of the medium and the like conditions. Typically, the agent is preferably added 1 to several times (e.g. added at initiation of the culture and additionally supplemented at the time of subculture or medium replacement) so as to obtain the peptide concentration in the medium of about 0.1 µM to 100 µM, preferably 0.5 µM to 20 µM (e.g. 1 µM to 10 µM).

The agent for inducing nestin expression (nestin-inducing synthetic peptide) described herein, namely the astrocyte-dedifferentiating agent (astrocyte-dedifferentiating synthetic peptide) may be used in combination with other agents for inducing nestin expression or other astrocyte-dedifferentiating agents, or used in combination with other methods for inducing nestin expression or other methods for dedifferentiating astrocytes.

Alternatively, the agent for inducing nestin expression (nestin-inducing synthetic peptide) described herein, namely the astrocyte-dedifferentiating agent (astrocyte-dedifferentiating synthetic peptide) in the form of, for example, a solution or an individual such as a tablet or a gel or a water-based jelly such as ointment may be given to a patient (i.e. a living body) at a desired amount. Examples of a method for administration include intravenous or intracranial injection and oral administration. Thereby, high nestin expressing cells (i.e. nestin-expressing neural stem cells) can be produced (generated) in astrocytes at or around an affected site or in astrocytes that may migrate into an affected site. By utilizing the neural stem cells, nerve function which has been damaged due to various neurological diseases or trauma may be effectively restored. For example, neurological diseases and trauma such as Parkinson's disease, cerebral infarction, Alzheimer's disease, paralysis due to spinal cord injury, cerebral contusion, amyotrophic lateral sclerosis, Huntington's disease, brain tumour and retinal degeneration may be treated by a regenerative therapeutic approach. The agent may also be used as a drug composition contributing to regenerative therapy of the neurological diseases and trauma.

Alternatively, by using the agent for inducing nestin expression (nestin-inducing synthetic peptide) described herein, namely the astrocyte-dedifferentiating agent (astrocyte-dedifferentiating synthetic peptide), high nestin expressing cells (nestin-expressing neural stem cells) can be effectively produced from an astrocyte culture. Namely, by transferring high nestin expressing cells (nestin-expressing neural stem cells) into an affected site (i.e. into a body of a patient) effectively produced in vitro by employing the method for producing high nestin expressing cells (the method for producing nestin-expressing neural stem cells) described herein, neurological diseases and trauma such as Parkinson's disease, cerebral infarction, Alzheimer's disease, paralysis due to spinal cord injury, cerebral contusion, amyotrophic lateral sclerosis, Huntington's disease, brain tumour and retinal degeneration may be treated by a regenerative therapeutic approach. The neural stem cells produced in vitro by the method for producing high nestin expressing cells described herein, namely the method for producing nestin-expressing neural stem cells may be used as a medical material contributing to regenerative therapy.

A number of Examples of the present invention is hereinafter described. However, it is not intended to limit the present invention to the Examples.

Example 1: Peptide Synthesis

Synthetic peptides having amino acid sequences SEQ ID NOs: 7 to 9 were manufactured with the peptide synthesiser described hereinbelow. In the following descriptions, the synthetic peptides are denoted as samples 1 to 3 according to the SEQ ID NOs. Table 1 indicates information on the amino acid sequences and the like of the synthetic peptides.

TABLE 1

| Sample No. | Amino acid sequence | Total amino acid residues |
|---|---|---|
| 1 | SLQYLCRFVIRQYTR KKRTLRKNDRKKR (SEQ ID NO: 7) | 28 |
| 2 | NLQDLCRIKIRQCIG KKRTLRKNDRKKR (SEQ ID NO: 8) | 28 |
| 3 | TLHQQCIRVLKNNID KKRTLRKNDRKKR (SEQ ID NO: 9) | 28 |

As shown in Table 1, all peptides of the samples respectively have a membrane-penetrating amino acid sequence, i.e. an amino acid sequence (SEQ ID NO: 2) derived from LIM kinase 2, at the C-terminal side of the peptide chains.

The peptide (SEQ ID NO: 7) of sample 1 has an amino acid sequence (SEQ ID NO: 1) of 15 consecutive amino acid residues from the N-terminal of the BC-box in human SOCS6, i.e. a nestin-inducing peptide sequence, which flanks N-terminal of the amino acid sequence at the C-terminal side as described above.

The peptide (SEQ ID NO: 8) of sample 2 has an amino acid sequence of 15 consecutive amino acid residues from the N-terminal of the BC-box in human ASB7, which flanks N-terminal of the amino acid sequence at the C-terminal side as described above.

The peptide (SEQ ID NO: 9) of sample 3 has an amino acid sequence of 15 consecutive amino acid residues from the N-terminal of the BC-box in human Elongin A, which flanks N-terminal of the amino acid sequence at the C-terminal side as described above.

All peptides have a C-terminal amino acid of which carboxyl group (—COOH) is amidated (—CONH$_2$), and are linear peptides having 28 amino acid residues in total. All peptides were synthesized by carrying out solid phase synthesis (Fmoc method) using a commercially available peptide synthesiser (a product from Intavis AG) according to the instruction. As the present invention is not characterized by the mode of use of the peptide synthesiser per se, detailed explanation thereof is omitted.

Synthesised samples were dissolved in PBS (−) to prepare stock solutions having a peptide concentration of 1 mM.

Example 2: Evaluation Test of Nestin Expression Inducing Activity of Synthetic Peptides in Astrocytes Derived from the Hippocampus—1

Among the synthetic peptides obtained in Example 1, sample 1 (i.e. the nestin-inducing synthetic peptide of the present invention) was evaluated for nestin expression inducing activity by quantifying the expression level of the nestin gene. Cells used for the test were cultured cells of astrocytes derived from rat brain hippocampus (R-HiAs-521: available from Lonza). The evaluation test is detailed as follows.

The astrocytes derived from rat brain hippocampus were inoculated into a 6-well cell culture plate at a density of $1.0 \times 10^5$ cells/well. The medium used was an astrocyte growth medium (Astrocyte Growth Medium Bullet kit: available from Lonza, hereinafter referred to as "AG medium") and the cells were incubated overnight in a $CO_2$ incubator at 37° C. and 5% $CO_2$.

After the overnight incubation, the medium was replaced with an AG medium containing the peptide of sample 1 at the amount of 5 µM, and the incubation was continued under the same condition for 2 more days. A comparative example was carried out without addition of the peptide.

After the incubation was completed, cultured cells from each experimental sample were washed with Cold PBS (−), and total RNA was extracted and purified using a commercially available RNA extraction and purification kit (NUCLEOSPIN™ RNA/Protein kit: available from Macherey Nagel). All procedures were carried out in the absence of RNase according to the instruction attached to the kit. The purified RNA was quantified using Agilent 2100 Bioanalyzer (available from Agilent Technologies).

The purified RNA was subjected to qRT-PCR to examine the expression level of the nestin gene. A house-keeping gene used was Actin β. RT-PCR employed the two-step RT-PCR method and quantitative PCR employed the TAQ-MAN® method.

Specifically, the total RNA was used as a template in RT-PCR to synthesise cDNA (complementary DNA). In RT-PCR, a random primer (dN6) and an oligo(dT) 20 primer were used with a reverse transcriptase, SUPER SCRIPT® III (available from Life Technologies).

The cDNA obtained in RT-PCR was then used as a template for quantitative PCR. DNA polymerase used was FASTSTART TAQMAN® Probe Master (ROX) (available from Roche Applied Science) and probes used were Probe #67 (a probe for nestin, Product No. 4688660) and Probe #63 (a probe for Actin β, Product No. 4688627) from the Universal Probe Library (available from Roche Applied Science) adjusted at a final concentration of 200 nM. The thermal cycler used was ABI PRISM 7700 (available from Life Technologies). Quantitative PCR reaction was carried out under the conditions of incubation at 95° C. for 10 seconds followed by 45 cycles of 95° C. for 15 seconds, 62° C. for 20 seconds and 72° C. for 20 seconds. The primers used for quantitative PCR had the following sequences.

Nestin Gene

```
Sense:
                                       (SEQ ID NO: 10)
GTCCTTAGTCTGGAGGTGGCTACA Anti-sense:
                                       (SEQ ID NO: 11)
CCAGGTGTCTGCAACCGAGAGTTC
```

Actin β Gene

```
Sense:
                                       (SEQ ID NO: 12)
CCTGGCTCCTAGCACCATGAAG Anti-sense:
                                       (SEQ ID NO: 13)
GATAGAGCCACCAATCCACACAG
```

The expression level of the nestin gene in each experimental sample was corrected with the expression level of Actin β in each experimental sample. The results of quantification of the expression level of the nestin gene are shown in FIG. 1. The expression level of each gene is expressed as a value relative to the expression level of the gene in the sample without addition of the peptide being regarded as 1.

As shown in FIG. 1, the culture with addition of sample 1 showed a significant increase in expression of the nestin gene compared to the culture without addition of the peptide. This indicates that the nestin-inducing synthetic peptide (i.e. the agent for inducing nestin expression containing the peptide as an active ingredient) described herein is a peptide (composition) that can induce expression of or increase the expression level of nestin in astrocytes. It also indicates that the peptide (composition) may have astrocyte dedifferentiation activity.

Example 3: Evaluation Test of Nestin Expression Inducing Activity of Synthetic Peptides in Astrocytes Derived from the Hippocampus—2

Among the synthetic peptides obtained in Example 1, sample 1 (i.e. the nestin-inducing synthetic peptide of the present invention) was evaluated for nestin expression inducing activity by western blot analysis using an anti-nestin antibody. Cells used for the test were cultured cells of astrocytes derived from rat brain hippocampus (R-HiAs-521: available from Lonza). A comparative example was carried out without addition of the peptide. The evaluation test is detailed as follows.

In the same manner as in Example 2, the astrocytes derived from rat brain hippocampus were incubated in the presence of the peptide at a peptide concentration of 5 μM for 3 days. After the incubation was completed, cultured cells from each experimental sample were washed with Cold PBS (−), and total protein was extracted using a commercially available protein extraction and purification kit (NucleoSpin™ RNA/Protein kit: available from Macherey Nagel). All procedures were carried out in the absence of proteases according to the instruction attached to the kit. The concentration of the extracted protein was quantified using RC DC Protein assay (available from BIO RAD).

According to the SDS (sodium dodecyl sulphate)-polyacrylamide electrophoresis (SDS-PAGE) and western blot analysis as described below, expression of nestin and GFAP in each experimental sample was examined. An internal standard used in the series of procedures was the GAPDH protein.

Specifically, proteins obtained from each experimental sample and a molecular weight marker (MagicMark™ XP Western Protein Standard: available from Life Technologies) were injected to a well of an SDS-polyacrylamide gel (precast gel for electrophoresis: available from Oriental Instruments Co., Ltd.) and SDS-PAGE was carried out. Electrophoresis of nestin was carried out on a 7.5% SDS-polyacrylamide gel and electrophoresis of GFAP and the GAPDH protein was carried out on a 5-20% SDS-polyacrylamide gel.

The proteins separated by SDS-PAGE were transferred (blotting) onto a PVDF (polyvinylidene difluoride) membrane which was then blocked in Perfect-Block (available from MoBiTec) diluted to 5% in PBS (−) containing Tween 20™ (hereinafter referred to as PBST (−)).

Nestin, GFAP and the GAPDH protein were detected with primary antibodies, an anti-nestin antibody (murine, available from Merck Millipore), an anti-GFAP antibody (murine, available from Progen Biotechnik) and an anti-GAPDH antibody (murine, available from Merck Millipore) diluted 500-, 5000- and 10000-fold, respectively, in PBST (−) by the reaction for 1 hour at room temperature. The reaction at room temperature was then carried out for 1 hour with a secondary antibody, an HRP (Horseradish Peroxidase)-labelled anti-mouse IgG antibody (goat, available from Dako Cytomation) diluted 5000- to 10000-fold in PBST (−).

Figure 2:
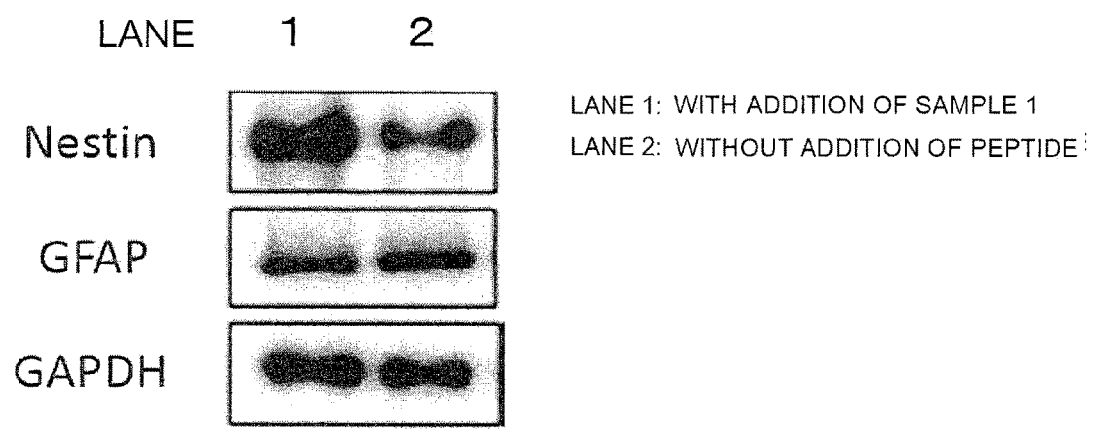
FIG. 2 is an image showing expression of nestin in astrocytes derived from the hippocampus cultured by adding a sample peptide (sample 1) according to one embodiment expressed as a result of western blot analysis.

Target proteins were then detected by reaction with the ECL prime Western blotting detection reagent (available from GE Healthcare) using the Luminescent image analyser LAS-3000 (available from Fujifilm Corporation). The results are shown in FIG. 2. Lane 1 is the result with addition of sample 1 and lane 2 is the result without addition of the peptide. In all experimental samples, expression of the internal standard, the GAPDH protein, was constant.

As shown in FIG. 2, the culture with addition of sample 1 showed a significant increase in expression of nestin compared to the culture without addition of the peptide. It was found that the culture with addition of sample 1 had expression of nestin 2 or more times higher than the culture without addition of the peptide. This indicates that the nestin-inducing synthetic peptide (i.e. the agent for inducing nestin expression containing the peptide as an active ingredient) described herein is a peptide (composition) that can induce nestin expression or increase the expression level of nestin in astrocytes. It also indicates that the peptide (composition) may have astrocyte dedifferentiation activity.

On the other hand, a difference in expression of GFAP was not confirmed between the culture with addition of sample 1 and the culture without addition of the peptide. Further, it was confirmed that in the culture with addition of sample 1, GFAP, of which expression was retained, and nestin, of which expression was induced by the peptide of sample 1, were co-expressed. Co-expression of nestin and GFAP is in conformity with expression pattern of the proteins in neural stem cells demonstrated in Non Patent Literature 4. This result also indicates that the nestin-inducing synthetic peptide (i.e. the agent for inducing nestin expression containing the peptide as an active ingredient) described herein has astrocyte dedifferentiation activity.

Although the data is not shown, it was confirmed that astrocytes in vivo do not express nestin, while various astrocytes cultured and subcultured under general culture conditions express nestin. This indicates that expression of nestin confirmed in the culture without addition of the peptide is an intrinsic protein expression pattern of cultured cells.

Example 4: Evaluation Test of Nestin Expression Inducing Activity of Synthetic Peptides in Astrocytes Derived from the Cerebral Cortex—1

Among the synthetic peptides obtained in Example 1, sample 1 (i.e. the nestin-inducing synthetic peptide of the present invention) was evaluated for nestin expression inducing activity by quantifying the expression level of the nestin gene. Cells used for the test were cultured cells of astrocytes derived from rat brain cerebral cortex (R-CxAs-520: available from Lonza). The evaluation test is detailed as follows.

The astrocytes derived from rat cerebral cortex were inoculated into a 6-well cell culture plate at a density of $1.0 \times 10^5$ cells/well. The cells were incubated in the AG medium overnight in a $CO_2$ incubator at 37° C. and 5% $CO_2$.

After the overnight incubation, the medium was replaced with an AG medium containing the peptide of sample 1 at the amount of 10 μM, and the incubation was continued under the same condition for 2 more days. A comparative example was carried out without addition of the peptide.

After the incubation was completed, total RNA was extracted from cultured cells from each experimental sample in the same manner as in Example 2.

The purified RNA was subjected to qRT-PCR in the same manner as in Example 2 to examine the expression level of the nestin gene. A house-keeping gene used was Actin β.

The expression level of the nestin gene in each experimental sample was corrected with the expression level of Actin β in each experimental sample. The results of quantification of the expression level of the nestin gene are shown in FIG. 3. The expression level of each gene is expressed as a value relative to the expression level of the gene in the sample without addition of the peptide being regarded as 1.

As shown in FIG. 3, the culture with addition of sample 1 showed a significant increase in expression of the nestin gene compared to the culture without addition of the peptide, as in Example 2. This indicates that the nestin-inducing synthetic peptide (i.e. the agent for inducing nestin expression containing the peptide as an active ingredient) described herein is a peptide (composition) that can induce expression of nestin in astrocytes. It also indicates that the peptide (composition) may have dedifferentiation activity of various astrocytes.

Example 5: Evaluation Test of Nestin Expression Inducing Activity of Synthetic Peptides in Astrocytes Derived from the Cerebral Cortex—2

Among the synthetic peptides obtained in Example 1, samples 1 to 3 were evaluated for nestin expression inducing activity by western blot analysis using an anti-nestin antibody. Cells used for the test were cultured cells of astrocytes derived from rat cerebral cortex (R-CxAs-520: available from Lonza). A comparative example was carried out without addition of the peptide. The evaluation test is detailed as follows.

In the same manner as in Example 4, the astrocytes derived from rat cerebral cortex were incubated in the presence of the peptide at a peptide concentration of 5 μM for 2 days. After the incubation was completed, total protein was extracted from cultured cells from each experimental sample in the same manner as in Example 3.

SDS-PAGE and western blot analysis were then carried out in the same manner as in Example 3 to examine expression of nestin and GFAP in each experimental sample. An internal standard used in the series of procedures was the GAPDH protein. The results are shown in FIG. 4.

Lanes 1, 2, 3 and 4 are the results without addition of the peptide, with addition of sample 2, with addition of sample 3 and with addition of sample 1, respectively.

As shown in FIG. 4, the culture with addition of sample 1 (i.e. lane 4) showed a significant increase in expression of the nestin compared to the culture without addition of the peptide. It was found that the culture with addition of sample 1 had expression of nestin 2 or more times higher than the culture without addition of the peptide. A difference in expression of GFAP was not confirmed between the culture with addition of sample 1 and the culture without addition of the peptide. Further, it was confirmed that in the culture with addition of sample 1, GFAP, of which expression was retained, and nestin, of which expression was induced by the peptide of sample 1, were co-expressed. These results indicate that the nestin-inducing synthetic peptide (i.e. the agent for inducing nestin expression containing the peptide as an active ingredient) described herein is a peptide (composition) that can induce expression of nestin in various astrocytes. It also indicates that the peptide (composition) may have astrocyte-dedifferentiating ability for various astrocytes.

On the other hand, a difference in expression of nestin or GFAP was not confirmed between the culture with addition of sample 2 or 3 and the culture without addition of the peptide. This indicates that the nestin expression inducing ability is not a common function of BC-box-related peptides (amino acid sequences derived from BC-boxes or modified peptides thereof) of SOCS proteins, but is a specific function of the nestin-inducing synthetic peptide (i.e. the agent for inducing nestin expression containing the peptide as an active ingredient) described herein.

Expression of nestin found in the culture without addition of the peptide and the cultures with addition of samples 2 and 3 is the protein expression intrinsic to cultured cells as described in Example 3.

In Examples 2 and 3, nestin expression inducing activity of the peptide of sample 1 was confirmed on astrocytes derived from the hippocampus, and in Examples 4 and 5, nestin expression inducing activity of the peptide of sample 1 was confirmed on astrocytes derived from the cerebral cortex. These results indicate that the nestin-inducing synthetic peptide (i.e. the agent for inducing nestin expression containing the peptide) has nestin expression inducing ability in various astrocytes and may have astrocyte-dedifferentiating ability for various astrocytes. To date, neural stem cells have been found only in limited regions such as SVZ and SGZ (Non Patent Literatures 1 to 6). The fact that astrocytes derived from regions other than SVZ and SGZ can be used for generation of neural stem cells provides an extremely high value in medical industry.

Example 6: Preparation of Granules

The synthetic peptide (nestin-inducing synthetic peptide) of sample 1 (50 mg), 50 mg of crystalline cellulose and 400 mg of lactose were mixed, followed by addition of 1 mL of a mixed solution of ethanol and water and further mixing. The mixed substance was granulated according to the standard method to obtain granules (a granular composition) containing the nestin-inducing synthetic peptide described herein as a principal component.

INDUSTRIAL APPLICABILITY

As described above, the nestin-inducing synthetic peptide described herein has nestin expression inducing ability which allows induction of nestin expression (or an increase of the expression level) in astrocytes, and thus can be used for the purposes of producing high nestin expressing cells derived from astrocytes and increasing the expression level of nestin in desired astrocytes. The high nestin expressing cells derived from astrocytes may function as neural stem cells. Thus, the method for producing high nestin expressing cells described herein can be utilised as, for example, a method for producing a material for regenerative therapy, and the agent for inducing nestin expression containing the nestin-inducing synthetic peptide as an active ingredient can be suitably used as a composition for regenerative therapy.

SEQUENCE LISTING FREE TEXT

SEQ ID NOs: 1 to 9 Synthetic peptides
SEQ ID NOs: 10 to 13 Primers

The invention claimed is:

1. A method for producing high nestin expressing cells derived from astrocytes, comprising:
   preparing an astrocyte culture; and
   supplying an agent for inducing nestin expression at least once to the astrocyte culture,
   wherein
   the agent for inducing nestin expression comprises a synthetic peptide comprising a nestin-inducing peptide sequence consisting of the following amino acid sequence:

```
                                              (SEQ ID NO: 1)
   SLQYLCRFVIRQYTR.
   ```

2. The method according to claim 1, further comprising selecting the high nestin expressing cells from the astrocyte culture to which the agent for inducing nestin expression has been supplied at least once.

3. The method according to claim 2, wherein the high nestin expressing cells are selected by using a cell sorter.

4. The method according to claim 1, wherein the synthetic peptide comprises a membrane-penetrating peptide sequence N-terminal or C-terminal to the nestin-inducing peptide sequence, wherein the membrane-penetrating peptide sequence comprises the amino acid sequence selected from the group consisting of SEQ ID NOS: 2, 3, 4, 5 and 6.

5. The method according to claim 1, wherein the synthetic peptide comprises the membrane-penetrating peptide sequence consisting of the following amino acid sequence:

```
                                              (SEQ ID NO: 2)
   KKRTLRKNDRKKR.
   ```

6. The method according to claim 1, wherein the synthetic peptide is composed of 28 or less amino acid residues in total.

7. The method according to claim 1, wherein the synthetic peptide comprises the following amino acid sequence:

```
                                              (SEQ ID NO: 7)
   SLQYLCRFVIRQYTRKKRTLRKNDRKKR.
   ```

* * * * *